United States Patent [19]

Timko

[11] Patent Number: 4,618,456

[45] Date of Patent: Oct. 21, 1986

[54] ETHYNYLATION OF 16-METHYL-17-KETO STEROIDS

[75] Inventor: Joseph M. Timko, Kalamazoo, Mich.

[73] Assignee: The Upjohn Company, Kalamazoo, Mich.

[21] Appl. No.: 604,091

[22] Filed: Apr. 26, 1984

Related U.S. Application Data

[63] Continuation-in-part of Ser. No. 591,631, Mar. 20, 1984, abandoned.

[51] Int. Cl.[4] ............................................. C07J 1/00
[52] U.S. Cl. ........................... 260/397.4; 260/397.45; 540/87; 540/88; 540/118
[58] Field of Search ..................... 260/397.4, 397.45

[56] References Cited

U.S. PATENT DOCUMENTS

| | | | |
|---|---|---|---|
| 2,272,131 | 2/1942 | Ruzicka | 260/397.4 |
| 2,723,280 | 11/1955 | Inhoffen et al. | 260/397.5 |
| 2,843,609 | 7/1958 | Colton | 260/397.5 |
| 2,877,240 | 3/1959 | Campbell et al. | 260/397.4 |
| 3,275,666 | 9/1966 | Siegmann | 260/397.5 |
| 3,470,217 | 9/1969 | Ginsig | 260/397.4 |
| 3,704,253 | 11/1972 | Stein et al. | 260/397.4 |
| 4,041,055 | 8/1977 | Shephard et al. | 260/397.3 |
| 4,055,562 | 10/1977 | Christiansen | 260/239.55 R |
| 4,320,236 | 3/1982 | Wiederkehr | 260/397.45 |
| 4,526,720 | 7/1985 | Van Rheenen et al. | 260/397.4 |

OTHER PUBLICATIONS

J. Am. Chem. Soc. 78, 2477 (1956).
J. Org. Chem. 34, 435 (1969).
J. Chem. Soc. 4765 (1956).
J. Mol. Structure 42, 251 (1977) J. B. Moffat.
J. Am. Chem. Soc. 98, 4778 (1976) A. Streitwieser.
Chem. Ind. (Milan) 42, 251 (1960).
Chem. Abst. 54, 19250 (1960).
J. Org. Chem. 43, 4679 (1978).
J. Med. Chem. 11, 924 (1968).
Steroids, Fieser and Fieser, Reinhold Pub. Co., New York, 1959, pp. 557-591.
Reagents for Organic Synthesis, vol. 1, Wiley, New York, 1967, p. 573.
Midland, Jour. Org. Chem. (1975) vol. 40, pp. 2250-2252.
Chemical Abstracts, vol. 97 (1982), Par, 182740z.

Primary Examiner—Elbert L. Roberts
Attorney, Agent, or Firm—Bruce Stein

[57] ABSTRACT

The process of the present invention transforms 16α- or 16β-methyl-17-keto steroids (I) to the corresponding 17α-ethynyl-17β-hydroxy-16α- or 16β-methyl steroids (II) without epimerization and loss of stereochemistry of the 16α- or 16β-methyl group.

23 Claims, No Drawings

ETHYNYLATION OF 16-METHYL-17-KETO STEROIDS

The present invention is a continuation-in-part of co-pending application Ser. No. 591,631, filed Mar. 20, 1984, now abandoned.

BACKGROUND OF THE INVENTION

Ethynylation of 17-keto steroids to produce commercially important 17α-ethynyl-17β-hydroxy steroids is well known to those skilled in the art. See, for example, U.S. Pat. Nos. 2,272,131, 2,843,609, 2,723,280, 2,877,240, 3,470,217, 4,041,055, Steroids by Fieser and Fieser, Reinhold Publishing Co., New York, 1959, pp. 557-591, and J. Am. Chem. Soc. 78, 2477 (1956).

The general method of ethynylation is to react the 17-keto steroid with dipotassium acetylide. The advantage of the dipotassium acetylide process is that it can be used with $\Delta^4$-3-keto steroids without having to protect the 3-keto group. However, that procedure cannot be used with 16α-methyl-17-keto, 16β-methyl-17-keto or 16-methylene-17-keto steroids for well known reasons. Commercially the ethynylation of 16α- or 16β-methyl- as well as 16-methylene-17-keto steroids is important because the 17α-ethynyl-17β-hydroxy-16α-methyl, 17α-ethynyl-17β-hydroxy-16β-methyl and 17α-ethynyl-17β-hydroxy-16-methylene steroids can be transformed to dexamethasone, betamethasone and melengestrol acetate.

Metallo-acetylides other than dipotassium acetylide are known. Monosodium acetylide is known, see U.S. Pat. No. 3,470,217 and R. J. Tedeschi, et al., J. Org. Chem. 34, 435 (1969). Mono- and bis-magnesium acetylides are known, see L. Skattebol, et al., J. Chem. Soc. 4765 (1956). Although the use of magnesio-acetylides has been reported for 17α-ethynyl introduction, substantial dimer formation results with both mono- and bis-magnesioacetylides, see U.S. Pat. No. 3,704,253.

Lithioacetylide reagents exhibit substantially different reactivity in many cases from other metallo-acetylides. This fact and the ready availability of n-butyllithium has resulted in the extensive use of these reagents in syntheses. The covalent nature of the carbon-lithium bond has been the subject of many theoretical and experimental investigations, see, for example, J. B. Moffat, J. Mol. Structure 42, 251 (1977) and A. Streitwieser, et al., J. Am. Chem. Soc. 98, 4778 (1976).

M. M. Midland in J. Org. Chem. 40, 2250 (1975) reported reacting n-butyllithium with acetylene in THF at low temperature ($< -70°$) and in dilute solution to produce monolithium acetylide. Monolithium acetylide is a valuable reagent for the preparation of ethynyl carbinols and terminal acetylenes, see Fieser and Fieser, Reagents for Organic Synthesis, Vol. 1, Wiley, New York, 1967, p 573. Midland found that warming or attempting to generate a more concentrated solution resulted in disproportionation to the insoluble dilithium acetylide and acetylene. This disproportionation is an important disadvantage and occurs in the absence of a complexing agent, see Corbellini et al., Chem. Ind. (Milan) 42, 251 (1960) and Chem. Abstr. 54, 19250 (1960). To reduce or prevent the disproportionation the monolithium acetylide is usually prepared in liquid ammonia, which presumably serves as an appropriate complexing agent. An amine such as ethylenediamine can also be used to stabilize monolithium acetylide. Ethylenediamine so greatly stabilizes monolithium acetylide that monolithium acetylide is sold commercially as an ethylenediamine complex. Ethylenediamine while stabilizing monolithium acetylide to the point it can be sold commercially actually reduces the reactivity to the point it is not useful for many ethynylation procedures.

The addition of a lithiated acetylene species to a 16β-methyl-17-ketone in 92% yield was reported by G. Neef, et al., in J. Org. Chem. 43, 4679 (1978) without giving any experimental data but stating, "The ethynylations were performed according to the procedure of Phillips..." The procedure of Phillips is set forth in J. Med. Chem. 11, 924 (1968). The results reported by Neef could not be reproduced; the Phillips procedure consistently gave large amounts (greater than 20%) of irreversible enolization. Neef also reported the addition of a lithiated acetylene species to a 16α-methyl-17-keto steroid. The yield Neef reported (72%) is more in keeping with the observed irreversible enolization.

U.S. Pat. No. 4,055,562 used monolithium acetylide to ethynylate 17-keto steroids unsubstituted in the $C_{16}$ position. The monolithium acetylide was prepared by bubbling acetylene into THF held at $-70°$ under anhydrous conditions followed by addition of butyllithium. The 17-keto steroid was added to the unstabilized monolithium acetylide and the mixture stirred for 3 hr at $-70°$ to produce the 17α-ethynyl-17β-hydroxy steroid product.

U.S. Pat. No. 4,320,236 discloses the use of a monolithium acetylide-ammonia complex (which is well known to those skilled in the art) to ethynylate ketones at below about 30°. The examples in U.S. Pat. No. 4,320,236 disclose ethynylation reaction temperatures of $-50°$ to 10°. The unsaturated acyclic ketones ethynylated in U.S. Pat. No. 4,320,236 are very reactive whereas the steroidal 16-methyl-17-ketones are highly substituted sterically hindered cyclopentanones and therefore much less reactive.

The process of the present invention uses monolithium acetylide and obtains 17α-ethynylation in yields greater than 85% with no detectable isomerization of the 16α- or 16β-methyl groups, indicating less than 2% epimerization.

SUMMARY OF THE INVENTION

Disclosed is a process for the preparation of a $C_3$ protected form of a 17α-ethynyl-17β-hydroxy-16-methyl steroid (II A,C) which comprises (1) contacting a $C_3$ protected form of a 17-keto-16-methyl steroid (I A,C) with monolithium acetylide in a dry solvent at a temperature of about 0° or less (2) maintaining the reaction temperature at about 0° or less and (3) quenching with a quenching agent.

Further disclosed is a process for the preparation of a 17α-ethynyl-17β-hydroxy-16-methyl steroid (II B) which comprises (1) contacting a 17-keto-16-methyl steroid (I B) with monolithium acetylide in a dry solvent at a temperature of about $-20°$ or less (2) maintaining the reaction temperature at about $-20°$ or less; and (3) quenching with a quenching agent.

Also disclosed are 17α-ethynyl-3,17β-dihydroxy-16β-methylandrosta-3,5-diene 3-methyl ether, 17α-ethynyl-3,17β-dihydroxy-16β-methylandrost-5-ene 3-THF ether, 17α-ethynyl-3,17β-dihydroxy-16β-methylandrosta-3,5,9(11)-triene 3-methyl ether, 17α-ethynyl-17β-hydroxy-16β-methylandrost-4-en-3-one, 17α-ethynyl-17β-hydroxy-16β-methylandrosta-4,9(11)-dien-3-one, and 17α-ethynyl-17β-hydroxy-16β-methylandrosta-1,4,9(11)-trien-3-one.

DETAILED DESCRIPTION OF THE INVENTION

The 16α- and 16β-methyl-17-keto steroids (I) are well known to those skilled in the art or can be readily prepared by methods well known to those skilled in the art from known compounds. See, for example, U.S. Pat. Nos. 3,010,958, 3,039,528 and 3,704,253. For the 16β-methyl-17-keto steroids (I) P. deRuggieri, et al., Gazz. Chim. Ital. 91, 672 (1961) on page 678 disclosed a 3-step process for the transformation of a 17-keto steroid to the corresponding 16β-methyl-17-keto steroid (I) in about 40% yield. The yield of that reaction can be greatly increased, and it is preferred to prepare the 16β-methyl-17-keto steroids from 17-keto steroids by the process of U.S. Pat. No. 4,451,404.

The 17-keto steroids (I) starting materials are well known to those skilled in the art or can be readily prepared from known compounds by methods well known to those skilled in the art. For example, 17-keto steroids (I) where $R_6$ is methyl, α-fluoro and methylene are known, see U.S. Pat. Nos. 3,166,551, 2,838,942 and 3,980,778 respectively. 17-Keto steroids (I) with C-ring substitution are known, for example, 9α-hydroxy (U.S. Pat. No. 3,065,146), $\Delta^{9(11)}$ (U.S. Pat. No. 4,127,596), 11β-hydroxy and 11-keto (U.S. Pat. No. 2,867,630). Further, these steroids are known in the $C_3$ protected forms, for example, the enol ether (U.S. Pat. No. 3,516,991) and the 3-enamine (U.S. Pat. No. 4,216,159).

The 17-keto steroids (IA-IC) may or may not have to have the functionality at $C_3$ protected during the ethynylation reaction depending on the nature of the steroid A ring (A-C, see Charts B and C). For the $\Delta^4$-3-keto steroids (A), the $C_3$ ketone is protected as the enol ether (Aa), ketal (Ab), or enamine (Ac) as is well known in the art, see Chart C. The preferred enol ether (Aa) is the methyl or ethyl ether. The preferred ketal (Ab) is the ethylene ketal. The preferred enamines (Ac) are selected from the group consisting of pyrrolidine, morpholine and diethylamino amines. The enol ethers (a) are prepared by methods well known in the art, see J. Org. Chem. 26, 3925 (1961), Steroid Reactions, Edited by Carl Djerassi, Holden-Day, San Francisco 1963, page 42–45, and U.S. Pat. No. 3,516,991 (Preparation 1). The ketals (b) are also prepared by well known methods, see Steroid Reactions, supra, page 11–14. The 3-enamines (c) are also prepared by methods well known in the art, see U.S. Pat. Nos. 3,629,298 and 4,216,159 and Steroid Reactions, supra, page 49–53.

The $\Delta^{1,4}$-3-keto steroids (B) do not have to have the $C_3$ ketone protected.

The 3-hydroxy steroid (C) should have the 3β-hydroxyl group protected as the ether (Ca), see Chart C. The preferred blocking groups are the methyl, ethyl, tetrahydropyranyl (THP) and trimethylsilyl ethers.

Monolithium acetylide is known, see M. M. Midland, J. Org. Chem. 40, 2250 (1975) and U.S. Pat. Nos. 4,055,562 and 4,320,236.

The monolithium acetylide can be prepared in different ways which is of importance because the temperature used in preparation is dependent on the method of preparation.

The monolithium acetylide can be prepared by bubbling acetylene through an etheral solvent such as THF at about 20°–25° until no further weight gain occurs (about 0.6M in acetylene). An aliquot of this solution is cooled to about −60° and 4 equivalents (per equivalent of steroid) of an organo-lithium reagent such as n-butyllithium, methyllithium or phenyllithium are added with vigorous stirring to give a mixture which is about 0.57M in monolithium acetylide. Temperatures above about −10° and concentrations above about 0.8M in monolithium acetylide cause disproportionation to the insoluble dilithium acetylide. Therefore, slow addition of pre-cooled (−20° or less) organo-lithium reagent to very cold solution of acetylene in a dry solvent such as THF, diethyl ether, dioxane, and DME is preferred. It is preferred the temperature be kept at −80° to −25°, more preferably at −80° to −40°. If the organic solvent is at a temperature of −40° or warmer, the organo-lithium solution should be added slower using a higher stirring rate to facilitate heat transfer. The monolithium acetylide solution should be used immediately after preparing as letting it stand even at −78° for 6 hours may lower the yield 10%.

A stabilized monolithium acetylide is preferably used. It permits preparation of the monolithium acetylide at higher temperatures which is commercially advantageous. The stabilized monolithium acetylide is prepared in 3 alternative ways, two-pot (preferred), one-pot or in situ.

In the two-pot process, a sufficient quantity of acetylene is first dissolved in a suitable dry organic solvent. The temperature at which the acetylene can be dissolved in the dry organic solvent is not critical. The temperature affects the solubility and therefore the concentration of the acetylene. However, before the acetylene solution is contacted with the lithium complex it must be cooled to 0° or less. The nature of the organic solvent is not critical so long as it does not react with acetylene, organolithium compounds or amines. Suitable dry organic solvents include THF, dioxane, diethyl ether, t-butyl methyl ether and dimethoxyethane. The preferred solvent is THF. It is convenient for the organic solvent to be saturated with acetylene. Second, an organo-lithium compound is contacted with a stabilizing amine at 0° or less in a suitable dry organic solvent. Organo-lithium compounds include n-butyllithium, phenyllithium, and methyllithium, preferred is n-butyllithium. A stabilizing amine is an amine (primary, secondary or tertiary) which when reacted with an organo-lithium compound to form a lithium complex and/or corresponding lithium amide subsequently reacted with acetylene forms a stabilized monolithium acetylide which will not significantly disproportionate at 0° and below which is reactive towards 17-keto steroids. Stabilizing amines include N,N-diisopropyl ethyl amine, triethylamine, diisopropyl amine, t-butyl amine, diethylamine, dicyclohexylamine, hexamethyl disilazane, and pyrrolidine. Some amines such as pyrrolidine are only useful with some steroids such as 16β-methylandrosta-1,4,9(11)-triene-3,17-dione. Amines which are not operable include ethylenediamine and pyridine. Preferred is diisopropylamine. The same dry organic solvents useful to dissolve the acetylene in are also useful here. It is preferred that the same solvent or mixture of solvents be used for dissolving the acetylene in as for the reaction of the organo-lithium compound with the stabilizing amine. The reaction of the organo-lithium compound with a primary or secondary amine produces a lithium amide. A tertiary amine cannot produce a lithium amide and forms a complex, the nature of which is not known. Therefore, the reaction of an organo-lithium compound and a stabilizing amine will be considered to have produced a lithium complex. When the organo-lithium compound is added to the stabilizing amine it must be added slowly maintaining the temperature at about 25° or less. The reaction is complete in less than 30 min.

The third step of the two-pot process is contacting the lithium complex of step 2 with the acetylene solution of step 1 at 0° or less. It is preferred that the method of contacting be a slow addition of the lithium complex to the acetylene solution keeping the temperature at 0° or less. The reaction forming monolithium acetylide is complete in about 30 min.

In the two-pot process, the first two steps which are independent of each other can be performed in the reverse order. The organo-lithium compound can be reacted with the stabilizing amine prior to the dissolving of the acetylene in the dry organic solvent. All that is necessary is that both steps be independently performed and the temperature of both mixtures be 0° or less before they are combined in the third step.

The 16-methyl-17-keto steroid (I) to be ethynylated is added to the monolithium acetylide at 0° or less. The ethynylation reaction is complete in about 30 minutes. The 16-methyl-17-keto steroid (I) can be added as a solid, a slurry or as a solution. For convenience it is preferred that it be added as a solution. It should be added slowly as is known to those skilled in the art. Again, the same organic solvents used for steps 1 and 2 are useful for adding the material to be ethynylated to the monolithium acetylide. Again, it is preferable to use the same organic solvent as was used in steps 1 and 2. The ethynylated product is recovered by means well known to those skilled in the art.

In the one-pot process, the first step of dissolving the acetylene in a suitable dry organic solvent is the same as for the two-pot process. Second, the stabilizing amine is added to the acetylene solution at 0° or less. Third, the organo-lithium compound is added slowly to the mixture of the acetylene solution and the stabilizing amine again at 0° or less.

With the in situ process, the first step again is the same. Second, the 16-methyl-17-keto steroid (I) to be ethynylated is added to the acetylene solution at 0° or less. Third, the organo-lithium compound and the stabilizing amine are reacted to form the lithium complex as in the second step of the two-pot process. Finally, the lithium complex is added slowly to the mixture of the acetylene solution containing the 16-methyl-17-keto steroid (I) to be ethynylated at 0° or less and the monolithium acetylide is generated in situ.

While the above steps to prepare monolithium acetylide can be performed at 0° it is preferable to perform them at less than $-20°$, more preferable in a temperature range of about $-20°$ to about $-40°$. Reducing the temperature reduces the amount of disproportionation, thereby increasing the amount of monolithium acetylide available for ethynylation.

Regardless of how the monolithium acetylide is prepared (two-pot, one-pot or in situ) when it is contacted with the $C_3$ protected 17-keto-16-methyl steroids (I A,C) at about 0° or less or the unprotected $\Delta^{1,4}$-3-keto 17-keto-16-methyl steroids (IB) at about $-20°$ or less, the reaction time is very short, in the range of 5-60 min usually about 10-15 min.

The above discussion involves the temperatures at which the monolithium acetylide is prepared. The main advantage of using stabilized monolithium acetylide over non-stabilized monolithium acetylide is that it can be prepared and reacted at warmer temperatures. The reaction temperature of the monolithium acetylide with the 16α- and 16β-methyl-17-keto steroids (I) is usually about the same as the preparation temperature. If the reaction is performed above the decomposition temperature of the reagent, the yield will decrease. In the $\Delta^{1,4}$-3-keto series (B) the reaction temperature must be lower than in the protected $\Delta^4$-3-keto (A) or 3-hydroxy (C) series because one must have selectivity for the monolithium acetylide with the $C_{17}$-ketone over the unprotected $C_3$-ketone. For the $\Delta^4$-3-keto (A) and 3-hydroxy (C) steroids in their $C_3$-protected form the ethynylation reaction is performed at about $-10°$ or less, preferably at about $-20°$ or less, more preferably at about $-40°$ or less. For the $\Delta^{1,4}$-3-keto steroids (B) the ethynylation reaction is performed at about $-10°$ or less, preferably at about $-40°$ or less, more preferably at about $-70°$ or less.

With the $\Delta^{1,4}$-3-keto-16-methyl-17-keto steroids (IB) no $C_3$ protecting group is necessary. However, it is preferable to add at least one equivalent of lithium ion prior to contacting the 17-keto steroid (I) with the monolithium acetylide. The lithium ion helps keep the selectivity for the 17-ketone over the 3-ketone. The lithium ion is added as a lithium salt, for example, lithium chloride, lithium sulfate, etc. Preferred is lithium bromide or lithium perchlorate. Using the lithium ion with $\Delta^{1,4}$-3-keto-16-methyl-17-keto steroids (IB) permits the same yield and selectivity at $-40°$ as was obtained without the lithium ion at $-78°$.

Generally, slightly more than one equivalent of monolithium acetylide per equivalent of 16-methyl-17-keto steroid (I) is used. With the 16α-methyl and 16β-methyl-17-keto steroids (I) the more monolithium acetylide used up to 4 equivalents the better. Two equivalents are preferred and about four equivalents are more preferred.

When the acetylene addition is complete the excess acetylide is quenched or destroyed by reaction with a quenching agent which is any system such as water, saline or aqueous buffers depending on what final pH is desired. The quenching agent can be any system which protonates the acetylide, e.g. water, saline, buffers or non-aqueous systems containing protonating compounds, e.g. acetic acid, formic acid or other acid. Other quenching agents which are operable are those which will react with the acetylide such as acetone, methyl ethyl ketone or other ketones. The preferred quenching agent is acetone followed by aqueous acid. The 17α-ethynyl-17β-hydroxy-16-methyl steroids (II) are obtained or isolated from the reaction mixture by means well known to those skilled in the art. In the case of the $\Delta^4$-3-keto steroids (A) and 3-hydroxy steroid (C) the 17α-ethynyl-17β-hydroxy-16-methyl steroids (IIA and IIC) are isolated as the $C_3$ protected form. The $C_3$ protecting group is removed by means well known to those skilled in the art or the $C_3$ protecting group may be left on for further chemical modification of the 17α-ethynyl-17β-hydroxy-16-methyl steroid (II). Before the 17α-ethynyl-17β-hydroxy-16-methyl steroid (II) is isolated the $C_3$ protecting group can be hydrolyzed in situ so as to obtain the unprotected or free 17α-ethynyl-17β-hydroxy-16-methyl steroid by reaction with a proton source such as sulfuric acid or hydrochloric acid at $20°-25°$. The acid is added until the pH is less than 2. For example, if the 17-keto-16-methyl steroid (IA) is protected as the enol ether (a) the protecting group can be removed by acid so that the 17α-ethynyl-17β-hydroxy-16-methyl steroid (II) will be isolated in the free $\Delta^4$-3-keto form (A). The $\Delta^{1,4}$-3-keto steroids (B) are not protected and therefore the 17α-ethynyl-17β-hydroxy-16-methyl product (II) will be in the free or unprotected form. The C₃ protecting group is removed from the 3-hydroxy steroids (C) by reaction with a means for hydrolyzing the C₃ protecting group which in the case of the ethers (Ca) includes acids with a pKa of less than 4.0.

The reaction mixture is worked up by adding saline to the hydrolysis mixture which results in 2 phases. The organic phase is separated, washed, dried and concentrated to give the desired product. Alternatively the product may be knocked out by water addition and recovered by known procedures.

The 17α-ethynyl-17β-hydroxy-16-methyl steroids (II) are useful as intermediates in the preparation of 16-methyl-17α-hydroxyprogesterones and 16-methyl corticoids, see U.S. Pat. No. 4,041,055. For example, 17α-ethynyl-17β-hydroxy-16β-methylandrosta-1,4,9(11)-trien-3-one (Examples 7 and 8) is transformed to 17α,21-dihydroxy-16β-methylpregna-1,4,9(11)-triene-3,20-dione by the process of U.S. Pat. No. 4,041,055. This $\Delta^{9(11)}$-corticoid is transformed by known methods to the bromohydrin, 9β,11β-epoxide and finally to the corresponding 9α-fluoro-11β-hydroxy compound which is betamethasone (U.S. Pat. No. 3,485,854).

DEFINITIONS

The definitions and explanations below are for the terms as used throughout the entire patent application including both the specification and claims.

All temperatures are in degrees Centigrade.

TLC refers to thin-layer chromatograhy.

GLC refers to gas-liquid chromatography.

THF refers to tetrahydrofuran.

THP refers to tetrahydropyranyl.

Saline refers to an aqueous saturated sodium chloride solution.

p-TSA refers to p-toluenesulfonic acid.

NMR refers to nuclear (proton) magnetic resonance spectroscopy, chemical shifts are reported in ppm (δ) downfield from tetramethylsilane.

TMS refers to trimethylsilyl.

EEE refers to ethoxy ethyl ether [—O—CH(CH₃)OCH₂CH₃].

DME refers to dimethoxyethane.

TEA refers to triethylamine.

LDA refers to lithium diisopropylamide.

When solvent pairs are used, the ratio of solvents used are volume/volume (v/v).

Androstenedione refers to androst-4-ene-3,17-dione.

Betamethasone refers to 9α-fluoro-11β,17α,21-trihydroxy-16β-methylpregna-1,4-diene-3,20-dione.

Monolithium acetylide refers to LiC₂H and complexed forms thereof.

$R_3$ is alkyl of 1 thru 5 carbon atoms with the proviso that with the ketal (Ab), and the enamine (Ac), the $R_3$ groups can be the same or different and can be connected.

$R_3'$ is alkyl of 1 thru 3 carbon atoms, a TMS, THP or EEE group.

$R_6$ is a hydrogen or fluorine atom, methyl or methylene group. When $R_6$ is methylene, there is no 5-6 double bond in formula (A) or in formula (C).

$R_9$ is nothing, a hydrogen, fluorine or oxygen atom which makes the C-ring (a) $\Delta^{9(11)}$ when $R_9$ is nothing and
(b) 9β,11β-epoxide when $R_9$ is an oxygen atom.

$R_{11}$ is a hydrogen or oxygen atom, two hydrogen atoms or α- or β-hydroxyl group which makes the C-ring (a) $\Delta^{9(11)}$ when $R_{11}$ is a hydrogen atom,
(b) 9β,11β-epoxide when $R_{11}$ is an oxygen atom and ⋯ between C₁₁ and R₁₁ is a single bond, and
(c) a ketone when $R_{11}$ is an oxygen atom and ⋯ between C₁₁ and R₁₁ is a double bond.

⋯ is a single or double bond.

~ indicates that the attached atom or group can be in either the α or β configuration.

When the term "alkyl of ___ thru ___ carbon atoms" is used, it means and includes isomers thereof where such exist and are operable.

X is a hydrogen atom or nothing, when X is nothing, the ⋯ at C₃ is a double bond, when X is a hydrogen atom, the ⋯ at C₃ is a single bond.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants as well as reaction conditions and techniques.

EXAMPLE 1

17α-Ethynyl-3,17β-dihydroxy-16β-methylandrosta-3,5-diene 3-methyl ether (IIAa)

Acetylene is bubbled into dry THF at 20°–25° until the THF is saturated. This solution (112 ml, containing 67.2 mmoles of acetylene) is transferred to an oven-dried flask and cooled to −60°. With rapid stirring 4 equivalents of n-butyllithium (1.6M in hexane, 40 ml) are added dropwise with stirring. The resulting solution is warmed gradually to −25°. 3-Hydroxy-16β-methylandrosta-3,5-diene-17-one 3-methyl ether (IAa, 5 gm) is added. After 10 minutes at −25° the reaction is complete as measured by TLC giving the title compound.

EXAMPLE 2

17α-Ethynyl-17β-hydroxy-16β-methylandrost-4-en-3-one (IIA)

Hydrochloric acid (6N, previously degassed) is added to the 17α-ethynyl-3,17β-dihydroxy-16β-methylandrosta-3,5-diene 3-methyl ether (IIAa, Example 1) in the form of the reaction mixture of Example 1. The cooling bath is removed and the reaction is stirred for 30 minutes. TLC showed the hydrolysis is complete. Saline is added. The organic phase is separated, dried over sodium sulfate, and concentrated under reduced pressure to give a solid. The solid is triturated with methanol (5 ml) at 0° for 2 hours. The mixture is filtered and the solids washed with cold methanol, then dried to give the title compound. mp greater than 230°; NMR (CDCl₃) 0.87, 1.09, 1.19, 2.54 and 5.72 ppm.

EXAMPLE 3

17α-Ethynyl-3,17β-dihydroxy-16β-methylandrost-5-ene 3-THP ether (IICa)

Following the general procedure of Example 1 and making noncritical variations but producing the monolithium acetylide at −75° instead of −60°, and performing the ethynylation reaction at −30° rather than −25°, and using 3β-hydroxy-16β-methylandrost-5-ene-17-one 3-THP ether (ICa) as the starting material, the title compound is obtained.

EXAMPLE 4

17α-Ethynyl-3,17β-dihydroxy-16β-methylandrost-5-ene (IIC)

17α-Ethynyl-3,17β-dihydroxy-16β-methylandrost-5-ene 3-THP ether (IICa, Example 3) is dissolved in THF (25 ml) and methanol (20 ml) and p-TSA (0.25 g) is added. After stirring for 35 minutes at 20°−25° the reaction is complete as measured by TLC. Water is added and the solution concentrated under reduced pressure and extracted into methylene chloride. The methylene chloride layer is washed with half-saturated saline solution, dried over sodium sulfate, and concentrated under reduced pressure to give a solid. The solid is triturated with chloroform (5 ml) at 0° to give the title compound. mp 200°−204°; NMR (THF-$d_8$) 0.62, 0.83, 0.84, 2.56 and 5.1 ppm.

EXAMPLE 5

17α-Ethynyl-3,17β-dihydroxy-16β-methylandrosta-3,5,9(11)-triene 3-methyl ether (IIAa)

A solution of THF saturated with acetylene is prepared by sparging acetylene into THF until no further weight gain occurs. To 112 ml of this solution, cooled to −60°, is added dropwise over 30 minutes n-butyllithium (1.6M in hexane, 40 ml). The solution is warmed to −25° and then 3-hydroxy-16β-methylandrosta-3,5,9(11)-trien-17-one 3-methylether (IAa, 5.0 g) is added. After 10 minutes TLC indicated the reaction is complete, providing a solution containing the title compound.

EXAMPLE 6

17α-Ethynyl-17β-hydroxy-16β-methylandrosta-4,9(11)-dien-3-one (IIA)

Degassed hydrochloric acid (6N) is added to 17α-ethynyl-3,17β-dihydroxy-16β-methylandrosta-3,5,9(11)-triene 3-methyl ether (IIAa, Example 5) until the pH equals 1 and the solution is warmed to 0°. TLC analysis indicates the hydrolysis is complete after about one hour. The mixture is then poured into 5° water (120 ml). The THF is removed under reduced pressure and the aqueous solution extracted with methylene chloride. The organic phase is separated from the aqueous phase and the methylene chloride removed under reduced pressure to give a solid. The solid is triturated with cold methanol (5 ml, at 0° for 2 hours) to give title compound. mp 213°−218°; NMR (CDCl$_3$) 0.83, 1.1, 1.33, 2.57, 5.57 and 5.73 ppm.

EXAMPLE 7

17α-Ethynyl-17β-hydroxy-16β-methylandrosta-1,4,9(11)-trien-3-one (IIB)

THF (50 ml) and diisopropylamine (40 ml) are mixed and cooled to −20°. Slowly n-butyl lithium (1.6M in hexane, 195 ml) is added with cooling maintaining the temperature in the range of −22° to −18°. When addition is complete the lithium diisopropyl amide is maintained at −20°.

THF (360 ml) is saturated with acetylene by bubbling acetylene thru the THF at −20° to −15°. The acetylene saturated THF is then cooled to −25°.

The lithium diisopropyl amide prepared above is added dropwise to the acetylene maintaining the reaction temperature less than −10°. When the lithium diisopropyl amide addition is complete, the monolithium acetylide is cooled to less than −40°.

16β-Methylandrosta-1,4,9(11)-triene-3,17-dione (IB, U.S. Pat. No. 3,010,958, 20 g) is added in THF (60 ml) to the lithium acetylide at −40°. When the reaction is complete, acetone (24 ml) is added. The mixture is warmed while bubbling nitrogen thru the slurry to remove excess acetylene. Water (25 ml) is slowly added. Water (105 ml) is then added more quickly creating two phases which are separated. The aqueous phase is washed with THF (50 ml); the organic phases (pH is 9) are combined, washed with aqueous sulfuric acid and concentrated to 350 ml. Heptane (200 ml) is added, the mixture heated to 80° and held for 30 min. The mixture is cooled slowly to 30° and then to 18° for one hr. The mixture is filtered, the solid washed with heptane (20 ml) and then dried under reduced pressure with heat to give the title compound.

EXAMPLE 8

17α-Ethynyl-17β-hydroxy-16β-methylandrosta-1,4,9(11)-trien-3-one (IIB)

THF (315 ml) and diisopropylamine (122 g) are mixed and cooled to −30°. n-Butyllithium (480 g) is added slowly to form LDA maintaining the temperature at −20±1°.

THF (1.36 l) is cooled to −20° and acetylene (100 g) is dissolved in the THF using a nitrogen sweep (for safety reasons). The mixture is cooled to less than −25° and the LDA mixture is added slowly keeping the temperature less than −20°. The entire monolithium acetylide mixture is cooled to −45°.

16β-Methylandrosta-1,4,9(11)-triene-3,17-dione (IB, U.S. Pat. No. 3,010,958, 70 g) is dissolved in THF (260 ml) and cooled to 20°−22°.

The steroid mixture is added to the monolithium acetylide keeping the pot temperature at −40°, the addition is complete in 10 min or less. When the reaction is complete (about 10 min at −40°) the reaction mixture is quenched with acetone (106 ml) in water (35 ml) keeping the temperature at less than −35°. The mixture is sparged with nitrogen. Water (480 ml) is added and the mixture warmed to 45°. The mixture is degassed under reduced pressure for 30 min monitoring the acetylene by GLC and then cooled to about 25° to facilitate removal of excess acetylene.

The reaction mixture is worked up as in Example 7 to give the title compound.

EXAMPLE 9

9β,11β-Epoxy-17α,21-dihydroxy-16β-methylpregn-4-ene-3,20-dione (U.S. Pat. No. 3,725,392)

Following the general procedure of U.S. Pat. No. 4,041,055 (Examples 37, 44, 51 and 66) and starting with 17α-ethynyl-17β-hydroxy-16β-methylandrosta-4,9(11)-dien-3-one (Example 6), 17α,21-dihydroxy-16β-methylpregna-4,9(11)-diene-3,20-dione is obtained which by methods well known to those skilled in the art is transformed (epoxidized) to give the title compound.

EXAMPLE 10

9α-Fluoro-11β,17α,21-trihydroxy-16β-methylpregna-1,4-diene-3,20-dione betamethasone (U.S. Pat. No. 3,485,854)

Following the general procedure of U.S. Pat. No. 4,041,055 (Examples 37, 44, 51 and 66) and starting with 17α-ethynyl-17β-hydroxy-16β-methylandrosta-1,4,9(11)-trien-3-one (Example 7), 17α,21-dihydroxy-16β-methylpregna-1,4,9(11)-triene-3,20-dione is obtained which after reaction with HOBr, epoxidation and reaction with HF all by means well known to those skilled in the art produces the title compound.

EXAMPLE 11

17α-Ethynyl-17β-hydroxy-16β-methylandrosta-1,4,9(11)-trien-3-one (IIB)

Dry THF (5 l) is cooled to −20° and acetylene (0.27 kg) is dissolved in the THF at −20°. Diisopropylamine (880 ml) is added to the acetylene/THF solution. n-Butyllithium (1.6M, 3.88 l) is added to the mixture maintaining the temperature at −20° and stirred for 30 min. 16β-Methylandrosta-1,4,9(11)-triene-3,17-dione (IB) in (THF) is added to the reaction mixture at or below −20° and stirred for 20 min to give the title compound.

EXAMPLE 12

17α-Ethynyl-3,17β-dihydroxy-16α-methylandrosta-3,5,9(11)-triene 3-methyl ether (II Aa)

THF (47 ml) at 20°–25° is saturated with acetylene and then cooled to −73°. n-Butyllithium (1.6M in hexane, 9.5 ml) is added and the mixture stirred 30 min at −73° and then warmed to −30°. 3-Hydroxy-16α-methylandrosta-3,5,9(11)-trien-17-one 3-methyl ether (I Aa, 1 g) dissolved in THF (20 ml) is added. TLC shows the reaction is complete after 30 minutes. The mixture is poured in aqueous phosphate buffer (pH=7) and is extracted with ethyl acetate. The layers are separated, the organic phase is dried over sodium sulfate and concentrated under reduced pressure to give the title compound with no 16β-epimer visible by NMR.

I claim:

1. A process for the preparation of a $C_3$ protected form of a 17α-ethynyl-17β-hydroxy-16-methyl steroid of the formula

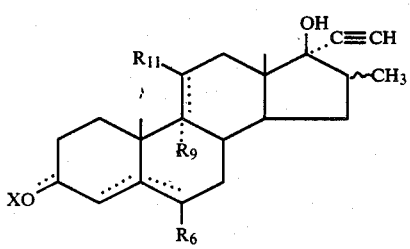
(IIA,C)

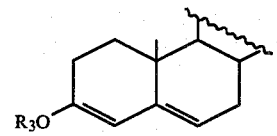
enol ether (Aa)

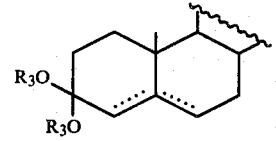
ketal (Ab)

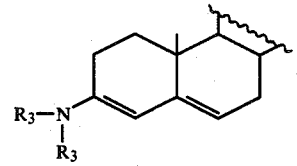
enamine (Ac)

with less than 2% epimerization which comprises
(1) contacting a $C_3$ protected form of a 17-keto-16-methyl steroid of the formula

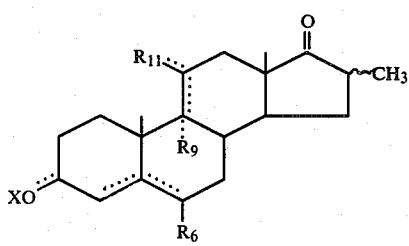
(IA,C)

with monolithium acetylide in a dry solvent at a temperature of about $-10°$ or less in the absence of ethylene diamine (2) maintaining the reaction temperature at about $-10°$ or less and
(3) quenching with a quenching agent where
$R_6$ is a hydrogen or fluorine atom, methyl or methylene group; when $R_6$ is methylene, there is no 5-6 double bond in formula (A) or in formula (C);
$R_9$ is nothing, a hydrogen, fluorine or oxygen atom which makes the C-ring
  (a) $\Delta^{9(11)}$ when $R_9$ is nothing and
  (b) $9\beta,11\beta$-epoxide when $R_9$ is an oxygen atom and $\rightleftharpoons$ between $C_{11}$ and $R_{11}$ is a single bond, and $\rightleftharpoons$
  (c) a ketone when $R_{11}$ is an oxygen atom and between $C_{11}$ and $R_{11}$ is a double bond;
X is a hydrogen atom or nothing, when X is nothing, the $\rightleftharpoons$ at $C_3$ is a double bond, when X is a hydrogen atom the $\rightleftharpoons$ at $C_3$ is a single bond;
$\rightleftharpoons$ is a single or double bond; and
$\sim$ indicates that the attached atom or group can be in either the $\alpha$ or $\beta$ configuration.

2. A process according to claim 1 where the 17-keto-16-methyl steroid (I) is a $\Delta^4$-3-keto steroid of the formula

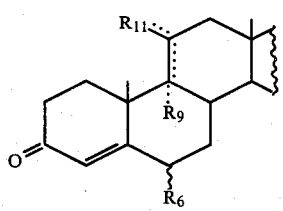
(A)

and the $C^3$ protected form is selected from the group consisting of or a $3\beta$-hydroxy-$\Delta^5$ steroid of the formula

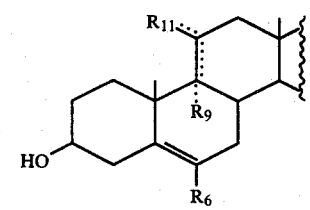
(C)

in its $C_3$ protected form

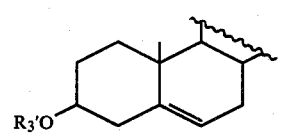
ether (Ca)

where
$R_3$ is alkyl of 1 thru 5 carbon atoms with the proviso that with the ketal (Ab), and the enamine (Ac), the $R_3$ groups can be the same or different and can be connected;
$R_3'$ is alkyl of 1 thru 3 carbon atoms, a TMS, THP or EEE group;
$R_6$ is a hydrogen or fluorine atom, methyl or methylene group; when $R_6$ is methylene, there is no 5-6 double bond in formula (A) or in formula (C);
$R_9$ is nothing, a hydrogen, fluorine or oxygen atom which makes the C-ring
  (a) $\Delta^{9(11)}$ when $R_9$ is nothing and
  (b) $9\beta,11\beta$-epoxide when $R_9$ is an oxygen atom;
$R_{11}$ is a hydrogen or oxygen atom, two hydrogen atoms or $\alpha$- or $\beta$-hydroxyl group which makes the C-ring
  (a) $\Delta^{9(11)}$ when $R_{11}$ is a hydrogen atom,
  (b) $9\beta,11\beta$-epoxide when $R_{11}$ is an oxygen atom and $\rightleftharpoons$ between $C_{11}$ and $R_{11}$ is a single bond, and
  (c) a ketone when $R_{11}$ is an oxygen atom and $\rightleftharpoons$ between $C_{11}$ and $R_{11}$ is a double bond; $\rightleftharpoons$ is a single or double bond; and ~ indicates that the attached atom or group can be in either the α or β configuration.

3. A process according to claim 1 where the dry solvent is selected from the group consisting of THF, dioxane, diethyl ether, t-butyl methyl ether, DME, and mixtures thereof.

4. A process according to claim 1 where the temperature is about −20° or less.

5. A process according to claim 1 where the temperature is about −40° or less.

6. A process according to claim 1 where the monolithium acetylide is stabilized by an amine.

7. A process according to claim 6 where the amine is selected from the group consisting of N,N-diisopropylethylamine, triethylamine, diisopropylamine, t-butylamine, diethylamine, dicyclohexylamine, and hexamethyl disilazane.

8. A process according to claim 1 where the quenching agent is a protic system selected from the group consisting of water, saline, aqueous buffers, methanol, ethanol, acetic acid, formic acid, acetone, methyl ethyl ketone and mixtures thereof.

9. A process according to claim 1 where greater than 1 equivalent of monolithium acetylide is used.

10. A process according to claim 1 where the 17α-ethynyl-17β-hydroxy-16-methyl steroid (II) is selected from the group consisting of 17α-ethynyl-3,17β-dihydroxy-16β-methylandrosta-3,5-diene 3-methyl ether, 17α-ethynyl-3,17β-dihydroxy-16β-methylandrost-5-ene 3-THP ether and 17α-ethynyl-3,17β-dihydroxy-16β-methylandrosta-3,5,9(11)-triene 3-methyl ether.

11. A process for the preparation of a 17α-ethynyl-17β-hydroxy-16-methyl steroid of the formula

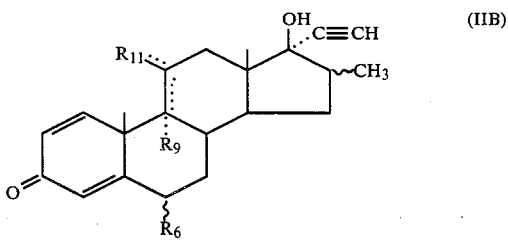

with less than 2% epimerization which comprises
(1) contacting a 17-keto-16-methyl steroid of the formula

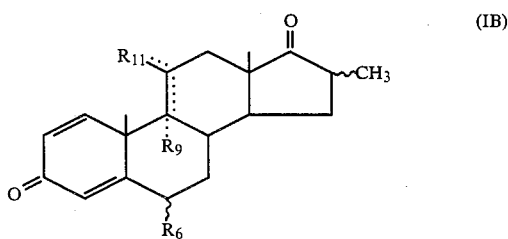

with monolithium acetylide in a dry solvent at a temperature of about −10° or less in the absence of ethylene diamine
(2) maintaining the reaction temperature at about −10° or less and (3) quenching with a quenching agent where
$R_6$ is a hydrogen or fluorine atom, methyl or methylene group; when $R_6$ is methylene, there is no 5-6 double bond in formula (A) or in formula (C);
$R_9$ is nothing, a hydrogen, fluorine or oxygen atom which makes the C-ring
 (a) $\Delta^{9(11)}$ when $R_9$ is nothing and
 (b) 9β,11β-epoxide when $R_9$ is an oxygen atom and ⋯ between $C_{11}$ and $R_{11}$ is a single bond, and
 (c) a ketone when $R_{11}$ is an oxygen atom and ⋯ between $C_{11}$ and $R_{11}$ is a double bond;
$R_{11}$ is a hydrogen or oxygen atom, two hydrogen atoms, or α- or β-hydroxyl group which makes the C-ring
 (a) $\Delta^{9(11)}$ when $R_{11}$ is a hydrogen atom,
 (b) 9β,11β-epoxide when $R_{11}$ is an oxygen atom and and ⋯ between $C_{11}$ and $R_{11}$ is a single bond, and
 (c) a ketone when $R_{11}$ is an oxygn atom and ⋯ between $C_{11}$ and $R_{11}$ is a double bond;
 is a single or double bond; and
~ indicates that the attached atom or group can be in either the α or β configuration.

12. A process according to claim 11 where the dry solvent is selected from the group consisting of THF, dioxane, diethyl ether, t-butyl methyl ether, DME, and mixtures thereof.

13. A process according to claim 11 where the temperature is about −40° or less.

14. A process according to claim 11 where the temperature is about −70° or less.

15. A process according to claim 11 where the monolithium acetylide is stabilized by an amine.

16. A process according to claim 15 where the amine is selected from the group consisting of N,N-diisopropylethylamine, triethylamine, diisopropylamine, t-butylamine, diethylamine, dicyclohexylamine, and hexamethyl disilazane.

17. A process according to claim 11 where the quenching agent is a protic system selected from the group consisting of water, saline, aqueous buffers, methanol, ethanol, acetic acid, formic acid, acetone, methyl ethyl ketone and mixtures thereof.

18. A process according to claim 11 where the 17α-ethynyl-17β-hydroxy-16-methyl steroid (II) is 17α-ethynyl-17β-hydroxy-16β-methylandrosta-1,4,9(11)-trien-3-one.

19. A process according to claim 11 where at least one equivalent of lithium ion is added prior to contacting the 17-keto steroid (IB) with the monolithium acetylide.

20. A process according to claim 19 where the lithium ion is added as lithium bromide, lithium perchlorate, lithium chloride or lithium sulfate.

21. A 17α-ethynyl steroid selected from the group consisting of 17α-ethynyl-3,17β-dihydroxy-16β-methylandrosta-3,5,9(11)-triene 3-methyl ether, 17α-ethynyl-17β-hydroxy-16β-methylandrosta-4,9(11)-dien-3-one, and 17α-ethynyl-17β-hydroxy-16β-methylandrosta-1,4,9(11)-trien-3-one.

22. A process according to claim 1 where there is no detectable isomerization.

23. A process according to claim 11 where there is no detectable isomerization.

* * * * *

UNITED STATES PATENT OFFICE
CERTIFICATE OF CORRECTION

Patent No. 4,618,456          Dated October 21, 1986

Inventor(s) Joseph M. Timko

It is certified that error appears in the above-identified patent and that said Letters Patent are hereby corrected as shown below:

Column 2, line 63, "3-THF" should read --3-THP--
Column 11, line 50, "      " should read --CHART A--
Column 11, line 54, "   $CH_3$" should read -- ...$CH_3$ --
Column 12, line 1, "      " should read --CHART B--
Column 12, line 31, "      " should read --CHART C--

Column 13, line 42, "bond, and ...." should read --bond, and--
Column 13, line 43, "atom and" should read --atom and ....--

Column 16, line 21, "   is a single" should read --.... is a single--

Signed and Sealed this

Twenty-second Day of September, 1987

*Attest:*

DONALD J. QUIGG

*Attesting Officer*     *Commissioner of Patents and Trademarks*

UNITED STATES PATENT OFFICE
CERTIFICATE OF CORRECTION

Patent No. 4,618,456                        Dated  October 21, 1986

Inventor(s) Joseph M. Timko

It is certified that error appears in the above-identified patent and that said Letters Patent are hereby corrected as shown below:

Column 13, line 5, (IIA,C):   "$R_{11}\diagdown$"  should read: --$R_{11}\diagdown$--

Column 14, lines 12-13 (Ab):  "$\diagup\!\!\diagdown$"  should read: --$\diagup\!\!\diagdown$--

Signed and Sealed this

Twenty-ninth Day of December, 1987

*Attest:*

DONALD J. QUIGG

*Attesting Officer*   *Commissioner of Patents and Trademarks*